US00PP11702P

United States Patent [19]

Bradford et al.

[11] Patent Number: Plant 11,702

[45] Date of Patent: Dec. 19, 2000

[54] NECTARINE TREE NAMED 'CANDY SWEET'

[76] Inventors: Lowell Glen Bradford, 12439 E. Savana Rd.; Norman G. Bradford, 11875 E. Savana Rd., both of Le Grand, Calif. 95333

[21] Appl. No.: 09/229,634

[22] Filed: Jan. 13, 1999

[51] Int. Cl.[7] ..... A01H 5/00

[52] U.S. Cl. ..... Plt./190

[58] Field of Search ..... Plt./190

[56] References Cited

U.S. PATENT DOCUMENTS

P.P. 3,165 5/1972 Anderson ..... Plt./192

*Primary Examiner*—Howard J. Locker
*Assistant Examiner*—Wendy A Baker

[57] ABSTRACT

The present invention relates to a nectarine tree, *Prunus persica*, and more particularly to a new and distinct variety broadly characterized by a large size, vigorous, self-fertile, productive and regular bearing tree. The fruit matures under the ecological conditions described approximately the last week in June, with first picking on Jun. 24, 1998. The fruit is uniformly large in size, subacidic and sweet in flavor, globose in shape, clingstone in type, very firm and crispy in texture, and mostly red in skin color. The variety was a first generation cross using 'Red Diamond' U.S. Plant Pat. No. 3,165) nectarine as the seed parent and an unnamed yellow flesh nectarine seedling as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'Candy Sweet'. The present variety was developed by us in 1992 in a cultivated area of our experimental orchard at Bradford Farms near Le Grand, Calif. in Merced County (San Joaquin Valley). It was a first generation cross using 'Red Diamond' (U.S. Plant Pat. No. 3,165) nectarine as the seed parent and an unnamed yellow flesh nectarine seedling as the selected pollen parent. Subsequent to origination of the present variety of nectarine tree, we asexually reproduced it by budding and grafting on Nemaguard (unpatented) rootstock, in the experimental orchard described above, and such reproduction of plant and fruit characteristics were true to the original plant in all respects.

The present variety is most similar to its seed parent, the 'Red Diamond', by producing yellow flesh nectarines that are mostly red in skin color, very firm in texture, and that ripen the last week in June, but is distinguished therefrom and an improvement thereon by having a showy instead of nonshowy blossom and by producing fruit that is much sweeter in flavor, that is clingstone instead of freestone, and that is larger in size.

BRIEF DESCRIPTION OF THE DRAWING

The accompanying photograph exhibits four whole fruits positioned to display the characteristics of the skin color and form, a sectioned fruit sliced parallel to the suture plane to reveal the flesh, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard shipping ripe on Jul. 2, 1998. All major color code designations are by reference to the Inter-Society Color Council, National Bureau of Standards. Common color names are also used occasionally.

Tree

Size: Large, reaching a height of 13' [3.96 meters] by the 5th year, including typical dormant pruning.

Vigor: Vigorous, responding typically to irrigation and fertilization. The plant should be grown on a standard commercial rootstock for production purposes.

Growth: Upright and dense.

Form: Vase formed.

Hardiness: Hardy with respect to typical central California winters.

Production: Productive, thinning usually necessary.

Fertility: Self-fertile.

Bearing: Regular bearer, with no alternate bearing observed.

Trunk:

- *Size*.—Medium, reaching a maximun diameter of 6" [152 mm.] after after 5 years of growth.
- *Texture*.—Very rough.
- *Bark color*.—Brownish gray [64. brGr].
- *Lenticels*.—Numerous. Color: Dark orange yellow [72. d.OY]. Typical Size: 3/16" to 7/16" [4.8–11.1 mm.].

Branches:

- *Size*.—Medium, typical of the species.
- *Texture*.—Smooth on 1st year wood, increasing roughness with age.
- *Color*.—1st Year Wood Topside: Grayish red [19. gy.R]. 1st Year Wood Underside: Vivid yellow green [115. v.YG]. Older Wood: Deep yellowish brown [75. deep yBr].
- *Lenticels*.—Numerous, small. Color: Light orange yellow [70. 1.OY]. Size: 1/16" to 1/4" [1.6–6.4 mm.].

Leaves:

- *Size*.—Large. Average Length: 6¼" [158.8 mm.]. Average Width: 1¾" [44.5 mm.].
- *Thickness*.—Medium.
- *Form*.—Elliptical.
- *Apex*.—Acuminate.
- *Base*.—Acute.
- *Surface*.—Smooth.

*Color.*—Dorsal Surface: Moderate olive green [125. m.OLG]. Ventral Surface: Moderate yellow green [120. m.YG].
*Margin.*—Finely serrate.
*Venation.*—Pinnately net veined.
*Petiole.*—Average Length: ½" [12.7 mm.]. Average Thickness: 1/16" [1.6 mm.]. Color: Light yellow green [119.l.YG].
*Stipules.*—2 per leaf bud, up to 6 at the growing tip. Average Length: ⅜" [9.5 mm.].
*Glands.*—Numbers: 2 to 4 per leaf. Position: Alternately positioned on petiole and base of blade. Size: Medium. Form: Reniform. Color: Light yellow green [119.l.YG].

Flower buds:
*Hardiness.*—Hardy with respect to central California winters.
*Diameter.*—Typically ⅜" [9.5 mm.] 1 week before bloom.
*Length.*—Typically ¾" [19.1 mm.] 1 week before bloom.
*Form.*—Free.
*Surface.*—Pubescent.

Flowers:
*Blooming period.*—Medium as compared with other varieties.
*Onset of bloom.*—One percent on Feb. 28, 1998.
*Duration of bloom.*—One to two weeks, dependent on ambient temperature.
*Type.*—Showy.
*Average diameter.*—¾" [44.5 mm.].
*Color.*—Moderate pink [5. m.Pk].
*Fragrance.*—None to slight.

FRUIT

Maturity when described: Hard shipping ripe, Jul. 2, 1998.
Date of first picking: Jun. 24, 1998.
Date of last picking: Jul. 7, 1998.
Size: Uniform, large.
*Average diameter axially.*—2⅝" [66.7 mm.].
*Average transversely in suture plane.*—2¾" [69.9 mm.].
*Typical Weight.*—6.35 ounces [180 grams].
Form: Globose, uniform, symmetrical.
*Longitudinal section form.*—Round to elliptical.
*Transverse section through diameter.*—Round.
Suture: A sharp groove very near the stem transforming to an inconspicuous line on the lateral surface and then becoming a shallow groove toward the apex with a marked depression beyond the pistil point.
Ventral surface: Rounded, lipped stronger on one side toward the apex.
Lips: Unequal.
Cavity: Flaring, slightly elongated in the suture plane, suture showing on one side, stem markings occasionally.
*Depth.*—½" [12.7 mm.].
*Breadth.*—1" [25.4 mm.].
Base: Rounded to truncate.
Apex: Rounded.
Pistil point: Apical, negligible in length, indented within the suture.
Stem: Medium.
*Average length.*—⅜" [9.5 mm.].
*Average width.*—3/16" [4.8 mm.].

Skin:
*Thickness.*—Medium.
*Texture.*—Medium.
*Tenacity.*—Tenacious to flesh.
*Tendency to crack.*—Slight.
*Color.*—Very dark red [17. v.d.R] over a strong reddish orange [35. s.rO] background, brilliant orange yellow [67. brill.OY] areas where sun protected, with abundant strong orange yellow [68. s.OY] freckling.

Flesh
*Color.*—Brilliant yellow [83. brill.Y] with some very minor vivid red [11. v.R] flecking toward the skin.
*Surface of pit cavity.*—Brilliant yellow [83. brill.Y] fibers breaking when twisted away from the stone.
*Amygdalin.*—Lacking.
*Juice.*—Moderate, rich.
*Texture.*—Firm, crisp.
*Fibers.*—Abundant, fine.
*Ripens.*—Slightly earlier at the apex.
*Flavor.*—Subacid and sweet, ranging from 15 to 19 brix.
*Aroma.*—Slight.
*Eating quality.*—Very good.

STONE

Type: Clingstone.
Form: Oval.
Base: Straight.
Apex: Acute.
Hilum: Narrow.
Sides: Equal.
Surface: Irregularly furrowed toward the apex, pitted near the base.
Ridges: Jagged toward the base.
Color: Light brown [57. 1.Br] when first removed from fruit.
Pit wall: ¼" [6.4 mm.] thick.
Average width: Approximately 1 1/16".
Average length: Approximately 1¼".
Tendency to split: Slight in wet season.
Kernel:
*Form.*—Oval.
*Taste.*—Bitter.
*Viable.*—Yes.
*Average width.*—9/16" [14.3 mm.].
*Average length.*—¾" [19.1 mm.].
*Skin color.*—Light orange yellow [70. l.OY] with deep yellowish brown [75. deep yBr] veins when first removed from stone.
*Pellicle color.*—Moderate yellowish brown [77. m.yBr].
*Amygdalin.*—Abundant.

USE

Market: Fresh and long distance shipping.
Keeping quality: Fruit quality observed to remain in good condition in excess of 28 days in cold room at 36° Fahrenheit [2° Celsuis].
Resistance to insects: No unusual susceptibilities noted.
Resistance to diseases: No unusual susceptibilities noted.

Althought the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed parent, the 'Red Diamond' (U.S. Plant Pat. No. 3,165), by producing yellow flesh nectarines that are mostly red in skin color, very firm in texture, and that ripen the last week in June, but is distinguished therefrom and an improvement thereon by having a showy instead of nonshowy blossom and by producing fruit that is much sweeter in flavor, that is clingstone instead of freestone, and that is larger in size.

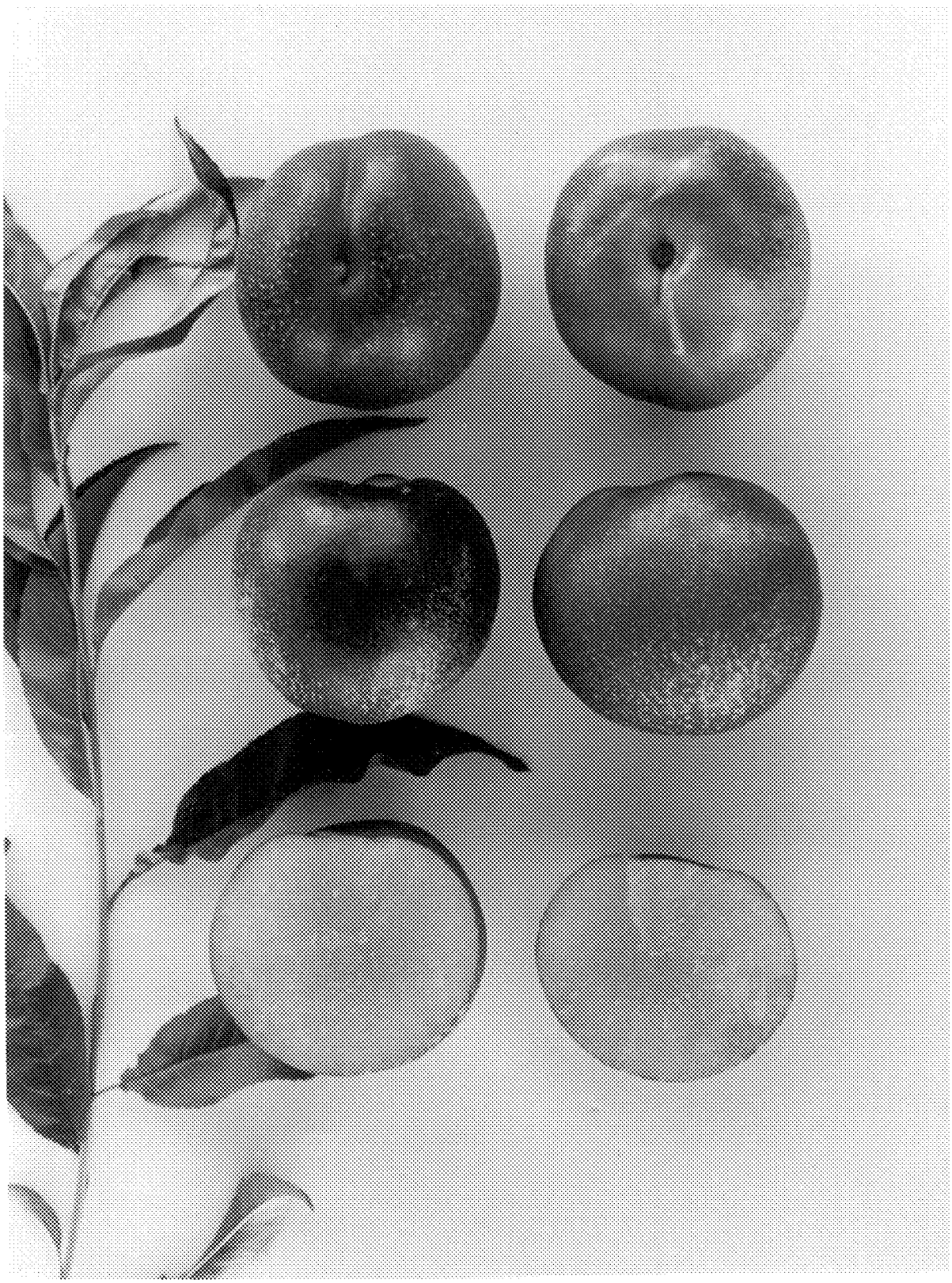

* * * * *